United States Patent [19]

Andrews et al.

[11] 4,024,467

[45] May 17, 1977

[54] METHOD FOR CONTROLLING POWER DURING ELECTROSURGERY

[75] Inventors: Stephen William Andrews; Stanley Woltosz, both of Rochester, N.Y.

[73] Assignee: Sybron Corporation, Rochester, N.Y.

[22] Filed: June 2, 1975

[21] Appl. No.: 582,593

Related U.S. Application Data

[62] Division of Ser. No. 488,281, July 15, 1974, Pat. No. 3,923,063.

[52] U.S. Cl. .............................. 332/14; 128/303.14; 128/303.17
[51] Int. Cl.² ...................... A61N 3/02; H03K 7/08
[58] Field of Search ................ 128/303.14, 303.17, 128/303.18; 332/14, 15, 10

[56] References Cited

UNITED STATES PATENTS

| | | | |
|---|---|---|---|
| 3,478,744 | 11/1969 | Leiter | 128/303.17 X |
| 3,658,067 | 4/1972 | Bross | 128/303.14 |
| 3,675,655 | 7/1972 | Sittner | 128/303.17 X |

Primary Examiner—Siegfried H. Grimm
Attorney, Agent, or Firm—Theodore B. Roessel; J. Stephen Yeo

[57] ABSTRACT

A control circuit for electrosurgical units establishes a particular output signal to patient electrodes in response to condition of the patient electrodes. The duty cycle of the output signal is reduced when the patient electrodes are not in contact with the patient so as to prevent unwanted cutting and the duty cycle is increased when both patient electrodes are in contact with the patient so as to maximize the coagulation effect.

The invention includes method of adjusting coagulation power by varying the duty cycle and not the amplitude of the output signal.

1 Claim, 2 Drawing Figures

METHOD FOR CONTROLLING POWER DURING ELECTROSURGERY

RELATED PATENTS

This is a division of Ser. No. 488,281, filed July 15, 1974 and now U.S. Pat. No. 3,923,063.

BACKGROUND OF THE INVENTION

This invention relates generally to rf modulation circuits and more particularly concerns rf modulation circuits for use in electrosurgical units. Electrosurgical units use high frequency (RF) power for cutting and coagulation of tissue under surgical conditions. The electrosurgical units apply a high frequency alternating current at power levels up to several hundred watts to electrodes usually consisting of an active probe and a dispersive plate generally known as a patient plate.

Two main types of current are provided, one for cutting and one for coagulation. The optimal cutting current is a continuous wave output from the electrosurgical unit. For smooth cutting a continuous arc is required between the active probe and the patient. Upon application of a high power continuous wave arc, the tissue cells volatize resulting in a smooth cutting action as the probe is moved along the surface of the tissue. To introduce hemostasis, the cutting current wave form is pulsed. The lower the duty cycle, the greater will be the amount of hemostasis and the less the cutting effect. Duty cycle is defined as the ratio of pulse on time to duration of the total pulse period times 100%. For effective coagulation a current with a duty cycle of approximately 20% to less than 5% is required. The longer off-time with a low duty cycle allows the tissue to cool off, so as to avoid volatization of cells, but enough power must be applied to sear off exposed blood vessels.

Both electrodes are available in various configurations to be selected by the surgeon according to the intended use. The active probe selected by the surgeon can range in size from a pair of forceps or a knife blade to a fine needle. The contact area of the probe and the type of tissue encountered are factors determining the amount of power necessary to effectively cut or coagulate the blood vessels contigous to the operating situs.

Electrosurgical units have previously used either spark gap or vacuum tube methods to achieve radio frequency levels of several hundred watts. For many years the generator used for producing a coagulation current was a spark gap type of generator. A spark gap oscillator can generate large peak powers at a low duty cycle while maintaining about 120 watts of average power. Spark gap methods, however, generate while noise whereas spectrum purity is desirable with electrosurgical units, particularly since electronic equipment is becoming more prevalent in hospitals. Vacuum tube units are capable of generating a power output of several hundred watts in the megahertz range, but, they generally also operate at low efficiency and have low reliability compared to presently available solid state circuitry. With the advent of solid state units it has been found that presently available transistors cannot generate the large amounts of peak power required under some conditions. Hence, so the duty cycle had to be increased to allow for adequate power, but, the larger duty cycle introduced a cutting effect in the coagulation mode. To minimize the cutting effect in the coagulation mode, a low duty cycle is required.

The amount of power required varies depending upon whether the active probe is arcing or in physical contact with the tissue and is also dependent upon the effective current density at the operating site, as determined by the contact area of the probe. All electrosurgical units on the market today employ amplitude control to vary the amount of coagulation power. Since a low duty cycle results in less cutting effect it would, therefore, be desirable to vary the duty cycle of electrosurgical units in response to load conditions as opposed to varying the amplitude control.

SUMMARY OF THE INVENTION

A pulse control circuit for an electrosurgical unit controls the duty cycle of a pulse modulated output signal. The output signal is applied to a plurality of patient electrodes. The voltage across the electrodes is sampled preferably by a capacitive voltage divider, and controls a threshold circuit. When the voltage between the patient electrodes exceeds predetermined level, the threshold circuit, preferably a Schmitt Trigger, generates a signal, which is applied to the modulator circuit of the electrosurgical unit. The presence or absence of the signal determines the duty cycle of the unit. The threshold circuit may be selectively connected with the modulator circuit so as to enable or disable its application according to use.

The electrosurgical unit may also be manually operated so as to control the average power by providing a pulse modulated output signal having a constant amplitude and varying the duty cycle of the output signal.

DETAILED DESCRIPTION OF THE DRAWINGS

Figure 1:
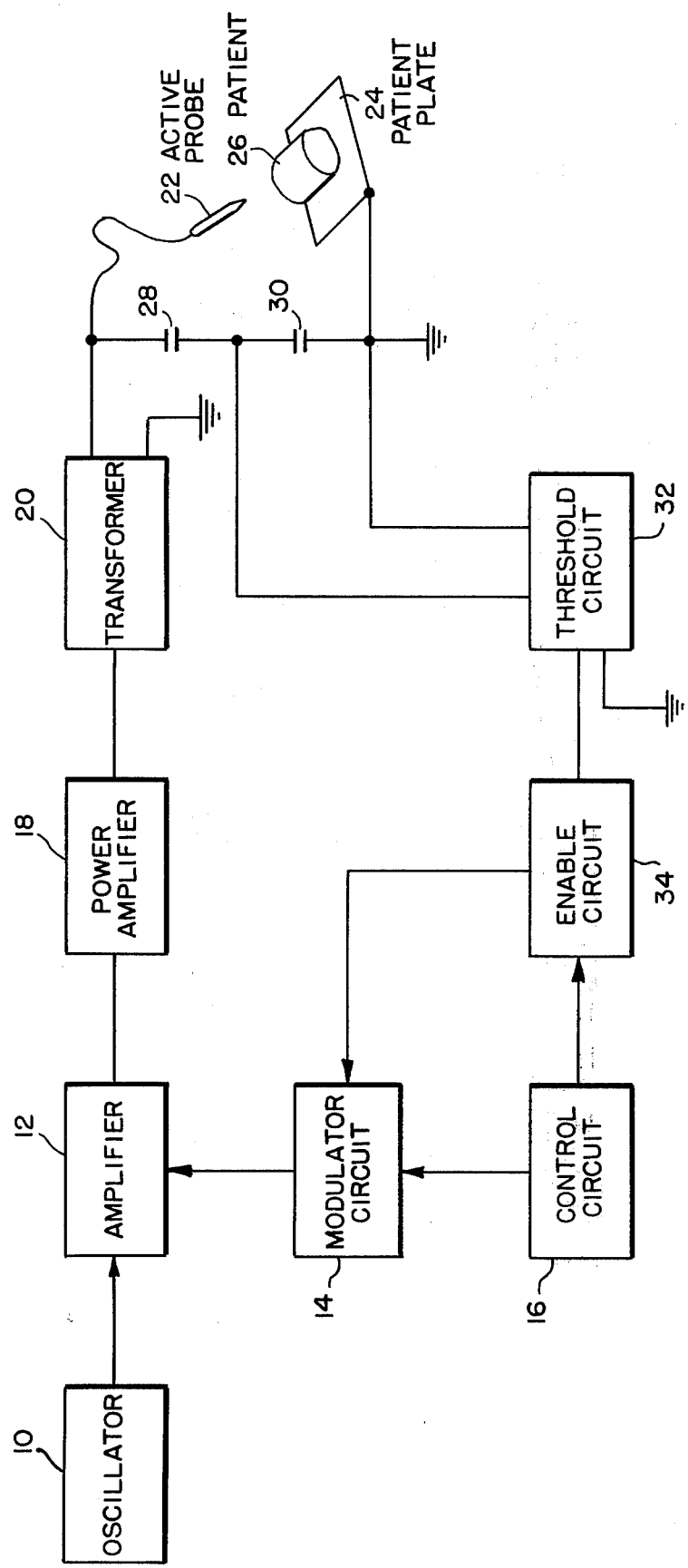
FIG. 1 is a block diagram of an electrosurgical unit which includes the pulse control circuit of the present invention.

FIG. 1 is a block diagram of an electrosurgical unit which includes the pulse control circuit of the present invention. An oscillator 10 generates a continuous wave RF signal. The RF signals are applied to the input of an amplifier 12. A modulator circuit 14 drives amplifier 12 on and off. The result is that the RF signal is pulse modulated by the amplifier 12 as driven by the modulator circuit 14. Control means 16 is used by the operator to select the desired modulation mode suitable for the surgical functions of cutting, cutting with hemostasis, and coagulation which are dependent upon the shape of output wave form and the duty cycle. A power amplifier 18 amplifies the modulated signals from amplifier 12 to a power level of approximately 400 watts. The amplifier signals are coupled from the power amplifier 18 by a transformer 20 to a pair of patient electrodes which include an active probe 22 and a patient plate 24. The patient 26 maintains continual contact with the patient plate 24 during the surgical operation. The active probe 22 is used for surgical procedures.

In accordance with a first feature of the invention, two capacitors 28 and 30 are connected in series between the active probe 22 and the patient plate 24. The purpose of the capacitors 28 and 30 is to act as a voltage divider so as to sample the voltage potential between the active probe 22 and the patient plate 24. It should be noted that other voltage dividers such as two resistors or other elements could also be used in this fashion instead of capacitors. The input terminals of a threshold circuit 32 are connected across the capacitor 30. It is seen that the voltage across the input of the threshold circuit 32 is the same voltage that appears across capacitor 30.

The property of the threshold circuit 32 is to generate an output signal when the input signal exceeds a present magnitude. The input voltage will be of low magnitude or high magnitude depending upon whether the active probe 22 is or is not in contact with the patient 26. When the active probe 22 is not in contact with the patient 26 the voltage across capacitor 30 will be in the high state and of sufficient magnitude to cause the threshold circuit 32 to thereby generate an output signal. The output signal from the threshold circuit 32 is connected to the modulation circuit 14 through an enabling circuit 34. The enabling circuit 34 is enabled by the control circuit 16. When the control circuit 16 is set by the operator so as to be in the coagulating mode the enable circuit 34 will be turned on so as to allow the output from the threshold circuit to reach the modulator circuit 14. In the coagulation mode, modulator circuit 14 can be adjusted to modulate the signal, for example, with 20% duty cycle in the absence of a threshold output signal. As will be described in further detail in a later portion of the specification the presence of a threshold signal has the affect of reducing the duty cycle of the RF signal, for example, from 20% to 5%. This reduction in duty cycle remains in effect until the active probe 22 becomes in contact with the patient 26 at which time the voltage across capacitor 30 and input signal to the threshold circuit 32 drops preventing the generation of the threshold output signal. The removal of the threshold output signal allows the modulated RF signal to return to the higher predetermined duty cycle of 20% in our example. The purpose of controlling of the duty cycle is to avoid cutting of the patient tissue while the electrosurgical unit is in the coagulation mode. It has been found that substantial cutting will occur when the active probe is not in contact with the patient but when at such a distance as to substain an arc between the active probe 22 and the patient 26. During coagulation it is desirable to reduce the duty cycle under arcing condition by reducing the average power dissipated at the operating site thereby reducing the cutting effect. When the active probe has made contact with the patient 26 a high power level is permissible as there is no longer an arc sustained so that unwanted cutting is eliminated. The higher average power is desirable to obtain the desired coagulation. When the control circuit 16 is switched to be in the cutting mode, the enable circuit 34 is disabled so as to prevent the threshold output signal from the threshold circuit 32 from reaching the modulation circuit 14, thereby the duty cycle of the RF signal remains constant regardless of active probe 22 contact with the patient 26. The duty cycle of the modulator 14 may be changed by the control circuit 16 to 100% during cutting mode to provide maximum average power under all cutting conditions. A reduction of this duty cycle while in the cutting mode will provide hemostasis in the cutting mode.

Figure 2:
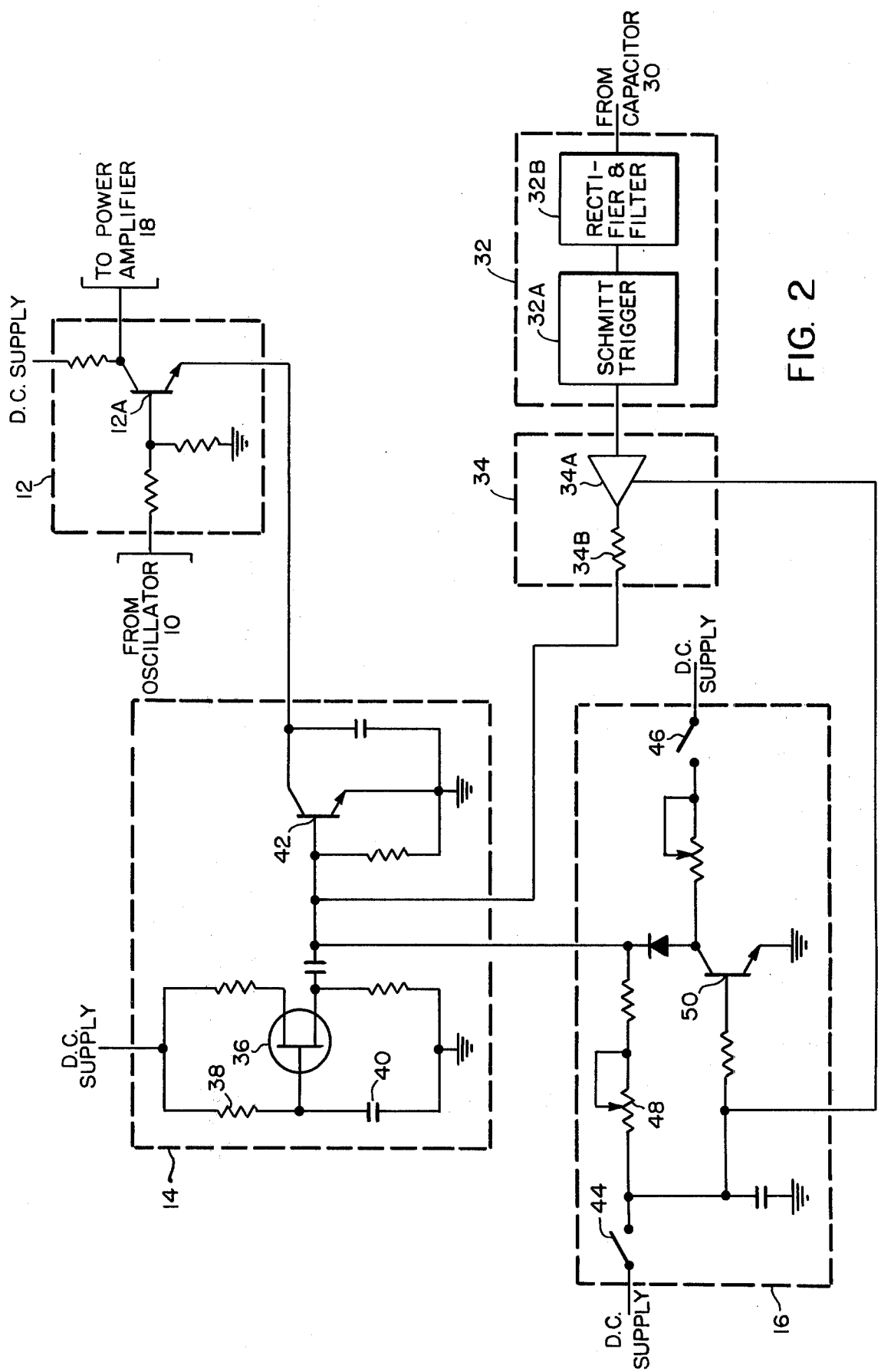
FIG. 2 is a schematic representation of the pulse control circuit of FIG. 1.

FIG. 2 is a schematic representation of the threshold circuit 32, the enable circuit 34, the modulation circuit 14, the input amplifier circuit 12 and the control circuit 16 of FIG. 1. The threshold circuit 32 includes a conventional Schmitt trigger circuit, however it is to be understood that other well known threshold circuits means may be used. A rectifier and filter circuit 32B converts the RF voltage from capacitor 30 to a DC level applied to the Schmitt circuit 32A. Schmitt circuits provide a signal during the time the input voltage attains or exceeds a particular magnitude. Thus, when the voltage across capacitor 30 of FIG. 1 exceeds a particular value an output signal will be generated by the Schmitt trigger. This output signal is connected through the enable circuit 34 to the modulator circuit 14. The enable circuit 34 allows the threshold signal to reach the modulator circuit 14 only when the electrosurgical unit is set to be in the coagulation mode. The enable circuit includes an isolation amplifier 34A of conventional design which is controlled by the coagulation switch 44. An electromechanical relay or similar device may be used as an enabling circuit means.

The modulating circuit 14 includes an unijunction transistor 36 connected in an oscillator circuit for generating a sawtooth voltage, the frequency of which is dependent upon resistor 38 and capacitor 40. The sawtooth voltage is applied to the base of a high gain transistor 42. Transistor 42 acts as a switch and is turned on and off depending upon the base voltage.

Control circuit 16 applies selected bias voltages to the base of transistor 42 offsetting the sawtooth voltage thereby controlling the amount of time transistor 42 is on. The magnitude of bias voltage is selected by a pair of foot switches 44 and 46. Switch 44 is closed for coagulation and switch 46 for cutting. When switch 46 is closed a bias voltage is applied to the base of transistor 42. The closing of switch 44 supplies a bias voltage to the base of transistor 42 and 50. The level of the bias voltage from coagulation 44 is determined by a potentiometer 48. As a safety measure, the closing of coagulation switch 44 turns on a transistor 50 which short circuits the bias voltage from cutting switch 46. Thus, the coagulation mode overides the cutting mode. Furthermore, when the coagulation switch 44 is closed the enable circuit 34 is enabled allowing the output signal from the threshold circuit 32 to be conducted through the enable circuit 34 to the base of transistor 42. The presence of the threshold signal voltage decreases the on time of transistor 42. In the absence of a threshold signal the on time of transistor 42 is determined by the adjustable second bias voltage as controlled by the potentiometer 48.

Amplifier 12 of FIG. 1 includes transistor 12A connected to transistor 42. The amplifier 12 is enabled only when transistor 42 is turned on. Therefore, it is seen that the RF signal from oscillator 10 is modulated by transistor 42 and has a pulse width of substantially the same duration as the on time of transistor 42. The total pulse repetition time is determined by resistor 38 and capacitor 40 and remains constant. Therefore, the duty cycle of the RF pulse is proportional to the pulse width of the threshold signal.

The pulse control circuit heretofore described automatically controls the duty cycle of the RF signal in response to active probe contact with the patient when the electrosurgical device is in coagulation mode. The invention prevents unwanted cutting during coagulation procedures by reducing the duty cycle and thereby reducing the average power when the electrosurgical unit is set for coagulation and when the active probe is not in contact with the patient. When the active probe is in contact with the patient the danger of cutting is reduced and the control circuit automatically increases the duty cycle thereby increasing the average power to maximize the coagulation effect. During cutting the pulse control circuit is disabled by setting the control circuit to cutting mode only so that a continuous wave is supplied to the probes.

In further accordance with the invention, the potentiometer 48 may be used to manually control the duty cycle without affecting the amplitude of the RF signal. This method enables the operator to adjust the electrosurgical unit to provide the minimum power necessary for coagulation under the operating conditions by using the lowest possible duty cycle. It has been found that this procedure reduces unwanted cutting when the electrosurgical unit is in the coagulating mode. This method may be used independently or in combination with the automatic pulse control circuit heretofore described.

We claim:
1. The method of controlling, during operating conditions, the average power of a pulse modulated output signal on an electrosurgical unit which comprises the following steps:
- selecting the mode of operation;
- providing a pulse modulated output signal having a constant amplitude; and
- varying the duty cycle of said output signal to obtain the amount of power desired for the particular operating conditions while allowing the amplitude to remain substantially constant.

* * * * *